(12) United States Patent
Partridge et al.

(10) Patent No.: US 6,762,314 B2
(45) Date of Patent: Jul. 13, 2004

(54) ORGANOMETALLIC COMPOSITIONS

(75) Inventors: Martin G Partridge, Stockton Tees (GB); Bruno F Stengel, Stockton on Tees (GB); John Ridland, Durham (GB)

(73) Assignee: Imperial Chemical Industries PLC, London (GB)

( * ) Notice: Subject to any disclaimer, the term of this patent is extended or adjusted under 35 U.S.C. 154(b) by 7 days.

(21) Appl. No.: 10/192,537

(22) Filed: Jul. 11, 2002

(65) Prior Publication Data

US 2003/0009043 A1 Jan. 9, 2003

Related U.S. Application Data

(63) Continuation of application No. PCT/GB00/04853, filed on Dec. 18, 2000.
(60) Provisional application No. 60/211,910, filed on Jun. 16, 2000.

(30) Foreign Application Priority Data

Jan. 12, 2000 (GB) .............................................. 0000569

(51) Int. Cl.⁷ .............................. C07F 7/00; C08K 5/06; C08G 18/22; C09J 4/00
(52) U.S. Cl. .......................... 556/40; 556/55; 264/109; 264/136; 156/331.4; 156/331.7; 528/56; 524/398
(58) Field of Search ................... 556/40, 55; 264/109, 264/136; 156/331.4, 331.7; 524/398; 528/56

(56) References Cited

U.S. PATENT DOCUMENTS

| | | | |
|---|---|---|---|
| 4,478,755 A | 10/1984 | Robbins | 260/429.5 |
| 5,646,200 A | 7/1997 | Duncan | 523/160 |
| 5,846,897 A | 12/1998 | Blank et al. | 502/150 |
| 6,288,200 B1 * | 9/2001 | Jung et al. | 528/56 |
| 6,288,255 B1 * | 9/2001 | Skinner | 556/55 |

FOREIGN PATENT DOCUMENTS

| | | |
|---|---|---|
| WO | WO 97/17388 | 5/1997 |
| WO | WO 00/02855 | 1/2000 |

* cited by examiner

*Primary Examiner*—Porfirio Nazario-Gonzalez
(74) *Attorney, Agent, or Firm*—Mayer Brown Rowe & Maw LLP

(57) ABSTRACT

An organometallic composition is described which comprises a complex of at least one orthoester of a metal having a formula $M(ROAcAc)_x(OR')_y$ in which M is selected from the group consisting of titanium, zirconium and hafnium; ROAcAc denotes an ester of an alochol ROH, in which R comprises an (optionally substituted) $C_{1-30}$ cyclic, branched or linear, alkyl, alkenyl, aryl or alkyl-aryl group or a mixture thereof, with acetoacetic acid; OR' is the residue of an alcohol R'OH in which R' comprises an (optionally substituted) $C_{7-30}$ cyclic, branched or linear, alkyl, alkenyl, aryl or alkyl-aryl group or a mixture thereof, and x and y are each in the range 1–3. The composition is useful as a curing agent for polyurethanes used in various applications.

20 Claims, No Drawings

ORGANOMETALLIC COMPOSITIONS

CROSS REFERENCE TO RELATED APPLICATIONS

This application is a continuation of PCT/GB00/04853, filed Dec. 18, 2000, and which further claims priority from British Application No. 0000569.4, filed Jan. 12, 2000, and from U.S. Provisional Application No. 60/211,910, filed Jun. 16, 2000. These applications in their entirety are incorporated herein by reference.

This invention relates to organometallic compositions based on Group IVB metals and which are useful in polyisocyanate compositions especially compositions for binding lignocellulosic material.

The use of organic polyisocyanates as binders for lignocellulosic material in the manufacture of sheets or moulded bodies such as waferboard, chipboard, fiberboard and plywood is well known. In a typical process the organic polyisocyanate, optionally in the form of a solution, dispersion or aqueous emulsion, is applied to the lignocellulosic material which is then subjected to heat and pressure. Isocyanates and polyisocyanates are also used in other applications in which it is necessary to effect curing of the compositions, e.g. in polyurethane coatings.

One suitable polyisocyanate composition is disclosed in PCT Application WO 97/17388. This composition comprises a Group IVB metal compound, preferably a titanium chelate, optionally in combination with a compatibilising compound and/or conventional release agents. Although these compositions perform well as binders for lignocellulosic material and provide good release performance, it is desirable to develop a more economical composition which provides improved stability on storage before use, together with good curing properties and excellent bonding strength when applied to the lignocellulosic material.

U.S. Pat. No. 5,846,897 discloses zirconium compounds with diketones or alkylacetoacetates which catalyse the isocyanate—hydroxy reaction having the chemical structure: Me (X1, X2, X3, X4) wherein Me is zirconium (Zr) or hafnium (Hf) and X1, X2, X3, and X4, are th same or different and selected from the group consisting of a diketone and an alkylacetoacetate having the structures: $R_1COCH_2COR_2$ and $R_1OCOCH_2COR_2$ wherein each of $R_1$ and $R_2$ is a branched or linear C1–C20 hydrocarbon and at least one of X1, X2, X3, and X4 is a diketone with structure (II) wherein the total number of carbons in $R_1+R_2$ is at least 4.

International Patent Application WO 00/02855 discloses that certain compounds of Group IVB metals can be used to cure isocyanate and polyisocyanate compositions and these compositions are very stable on prolonged storage and economical when used for binding lignocellulosic material. The compounds disclosed are complexes of titanium, zirconium and/or hafnium and a acetoacetate ester in which the molar ratio of Ti or Hf to acetoacetate ester is in the range 1:2.5 to 1:10 or the molar ratio of Zr to acetoacetate ester is in the range 1:4.5 to 1:10 and said acetoacetate ester is an ester of an alcohol containing 1 to 6 carbon atoms.

The physical properties of the materials used in this application are, of course an important factor in selecting appropriate compounds for use in curing the polyisocyanate compositions. One property which affects the handling and storage of the compounds is their flash point. It is desirable for the flash point to be relatively high for safety reasons whilst the melting point should be low enough for the material to be in liquid form under normal conditions for ease of handling.

It is an object of the present invention to provide an organometallic composition which is useful in the curing of polyisocyanate compositions and which has improved handling characteristics compared with the compositions of the prior art.

According to the invention, an organometallic composition comprises a complex of at least one orthoester of a metal having a formula $M(ROAcAc)_x (OR')_y$ in which (a) M is selected from the group consisting of titanium, zirconium and hafnium;

(b) ROAcAc denotes an ester of an alcohol ROH, in which R comprises an (optionally substituted) $C_{1-30}$ cyclic, branched or linear, alkyl, alkenyl, aryl or alkyl-aryl group or a mixture thereof, with acetoacetic acid;

(c) OR' is the residue of an alcohol R'OH in which R' comprises an (optionally substituted) $C_{7-30}$ cyclic, branched or linear, alkyl, alkenyl, aryl or alkyl-aryl group or a mixture thereof, and (d) x and y are each in the range 1–3 and x+y=4.

M is selected from the group consisting of titanium, zirconium and hafnium and the composition may comprise a mixture of these metals.

The titanium, zirconium or hafnium composition of the invention is described herein as a "complex". It is believed that some of the acetoacetate ester will be chemically bound to the metal (Ti, Zr and/or Hf) but some may be present as "free" ester. The exact proportions which are bound and free will depend partly upon the exact molar ratios present in the complex and which metal, or metals, are used, but it has been shown that the "free" ester does influence the properties, particularly the stability on storage of polyisocyanate compositions containing the complexes. Preferably the composition contains at least 0.5 moles of free ester per mole of metal, e.g. 0.5–10 moles, more preferably 1–5 moles free ester per mole of metal.

The molar ratio of titanium to total acetoacetate ester (i.e. free ester+complexed ester) in the composition is preferably in the range 1:2.5 to 1:10. When the metal is titanium, the molar ratio is preferably in the range 1:2.5 to 1:8 and more preferably in the range 1:3 to 1:6. When the metal is hafnium or zirconium, the molar ratio is preferably 1:4 to 1:10 and more preferably 1:4 to 1:8, hafnium or zirconium to total acetoacetate ester. For all metals mentioned, the complexes of the invention contain at least one alkoxide group and at least one acetoacetate ester so that x and y are each in the range 1–3 and the total of x+y is 4. When the metal is titanium, both x and y are preferably 2.

Preferably, the complex is a complex of at least one of titanium and zirconium and most preferably M is titanium.

R comprises an (optionally substituted) $C_{1-30}$ cyclic, branched or linear, alkyl, alkenyl, aryl or alkyl-aryl group or a mixture thereof. The preferred acetoacetate esters for preparing the complexes include ethyl acetoacetate, methyl acetoacetate, but esters of higher alcohols, e.g. $C_{7-30}$ preferably $C_{7-12}$ may be used, e.g. cetyl acetoacetate. The use of esters of higher alcohols is particularly preferred when the complex is to be used in applications in which it is subjected to elevated temperatures, e.g. above the boiling point of EtAcAc (b.p.=181° C.). It is not necessary that the acetoacetate esters are prepared by reacting the alcohol ROH with acetoacetic acid or a derivative thereof, since it is well known that esters may be made by other methods, e.g. by transesterification of another ester. Therefore the term "ester of an alcohol ROH in which R is an (optionally substituted) $C_{1-30}$ alkyl group with acetoacetic acid" as used herein is not to be taken to limit the ester to compounds made or obtainable by direct esterification of the acetoacetic acid with the alcohol. The complex can be prepared from more than one acetoacetate ester but preferably only one acetoacetate ester is present in the complex.

Preferred substituents on the R group, include halogens, especially bromine, chlorine or fluorine atoms since these substituted groups may enhance fire retardency properties.

The group R'O is an alkoxide group in which R' is a substituted or unsubstituted, $C_{7-30}$ cyclic, branched or linear, alkyl, alkenyl, aryl or alkyl-aryl group or a mixture thereof. It has been found that selection of such a group, i.e. having at least 7 carbon atoms produces metal complexes having desirable flash-point characteristics i.e. a flash point above 50° C. In preferred complexes of the invention R' is a $C_{8-12}$ alkyl group, e.g. 2-ethyl hexyl or other branched octyl species such as iso-octyl (2,4,4 trimethyl 1 pentanol) or mixed isomers of branched alkyl alcohol species such as the "Exxal™" products, e.g. Exxal 8, available from Exxon. Preferred complexes according to the invention include di(2-ethylhexyloxy)titanium bis(ethylacetoacetate) which has a flash point of about 68° C. and di(2,4,4-trimethyl-1-pentyloxy)titanium bis(ethylacetoacetate) which has a flash point of about 58° C., preferably in the presence of free acetoacetate ester. Preferred substituents on the R' group, include halogens, especially bromine, chlorine or fluorine atoms since these substituted groups may enhance fire retardency properties.

Typically, the complexes of titanium, zirconium or hafnium of the invention are prepared by transesterification by R'OH of titanium, zirconium or hafnium compounds having the general formula $M(OR")_y(ROAcAc)_x$ in which M is Ti, Zr or Hf and R" is a substituted or unsubstituted, cyclic, branched or linear, alkyl, alkenyl, aryl or alkyl-aryl group or mixtures thereof. For clarity, these compounds will be referred to hereinafter as "pre-complexes" Preferably, R" contains up to 6 carbon atoms and, more preferably, up to 4 carbon atoms. Generally, both OR" groups will be identical but alkoxides derived from a mixture of alcohols can be used and mixtures of alkoxides can be employed when more than one metal is present in the complex. In preferred pre-complexes, R" has less than 7 carbon atoms, esp 1–4 C atoms and is preferably methyl, ethyl, iso-propyl, n-propyl, t-butyl or n-butyl. We have found that preparation of compounds of formula $M(OR')_4$ when R' has >7 carbon atoms is very difficult and that it is therefore not practical to prepare the desired compounds by the apparently more obvious route of mixing together $M(OR')_4$ with an acetoacetate ester, and removing R'OH.

The pre-complexes, $M(OR")_y(ROAcAc)_x$, which form the starting material for the above-described preparation are conveniently prepared from $M(OR")_4$ where, as before, R" is a substituted or unsubstituted, cyclic, branched or linear, alkyl, alkenyl, aryl or alkyl-aryl group or mixtures thereof. Preferably, R" contains up to 6 carbon atoms and, more preferably, up to 4 carbon atoms. Generally, all four OR" groups will be identical but alkoxides derived from a mixture of alcohols can be used and mixtures of alkoxides can be employed when more than one metal is present in the complex. In preferred starting material compounds, R" is iso-propyl, n-propyl, t-butyl or n-butyl.

Suitable alkoxides include tetramethoxytitanium, tetraethoxytitanium, tetra-isopropoxytitanium, tetra-n-propoxytitanium, tetrabutoxytitanium, tetrapropoxyzirconium, tetrabutoxyzirconium, tetra-n-propoxyhafnium and tetra-n-butoxyhafnium. The pre-complexes can be readily prepared by mixing, for example, a metal alkoxide or condensed alkoxide with an appropriate amount of acetoacetate ester. Alcohol from the alkoxide will be displaced by the acetoacetate ester and, preferably, the displaced alcohol is removed by, for example, distillation. In a preferred method, 2 moles of acetoacetate ester per atom of Ti or 4 moles of acetoacetate ester per atom of Zr or Hf are added to an alkoxide or condensed alkoxide and the displaced alcohol is removed by distillation.

Alternatively, the pre-complexes can be prepared from condensed alkoxides of titanium, zirconium or hafnium. These compounds can be represented by the general formula $R"O[M(OR)_2O]_zR"$, wherein M and R" have the same meaning as discussed above and z is an integer. Generally, these condensed alkoxides consist of a mixture containing compounds of the above formula where z is an integer which may have a range of values. Preferably z has an average value in the range 2 to 16 and, more preferably, in the range 2 to 8. A condensed alkoxide is usually prepared by the controlled addition of water to an alkoxide, followed by removal of alcohol which is displaced. Suitable condensed alkoxides include the compounds known as polybutyl titanate, polybutyl zirconate and polyisopropyl titanate. Complexes of condensed alkoxides can also be prepared by forming a complex of an acetoacetate ester with an alkoxide, adding water to the complex and removing any by-product alcohol.

Alternatively, when an organometallic composition according to the invention is used in a polyisocyanate composition and it is desired to have free acetoacetate ester present, a product can be prepared according to the method outlined above and this can be mixed with a polyisocyanate. Any additional acetoacetate ester required can then be added to the polyisocyanate before or after the titanium, zirconium or hafnium compound has been added. This effectively results in the preparation of an organometallic composition in situ in the polyisocyanate composition. Other methods of preparing the composition of the invention will be apparent to a person skilled in this art.

The organometallic complexes of the invention are particularly useful as curing agents in polyisocyanate compositions and compositions suitable for use with the organometallic compositions of the present invention may be any organic polyisocyanate compound or mixture of organic polyisocyanate compounds, provided said compounds have at least 2 isocyanate groups. Organic polyisocyanates include diisocyanates, particularly aromatic diisocyanates, and isocyanates of higher functionality.

Examples of organic polyisocyanates for which the organometallic complexes of the present invention are useful curing agents include aliphatic isocyanates such as hexamethylene diisocyanate; and aromatic isocyanates such as m- and p-phenylene diisocyanate, tolylene-2,4- and tolylene-2,6-diisocyanate, diphenylmethane-4,4'-diisocyanate, chlorophenylene-2,4-diisocyanate, naphthylene-1,5-diisocyanate, diphenylene4,4'-diisocyanate, 4,4'-diisocyanate-3,3'-dimethyl-diphenyl, 3-methyldiphenylmethane4,4'-di-isocyanate and diphenyl ether diisocyanate; and cycloaliphatic diisocyanates such as cyclohexane-2,4- and -2,3-diisocyanate, 1-methylcyclohexyl-2,4- and -2,6-diisocyanate and mixtures thereof and bis-(isocyanatocyclohexyl)methane and triisocyanates such as 2,4,6-triisocyanatotoluene and 2,4,4-tri-isocyanatodiphenylether.

Modified polyisocyanates containing isocyanurate, carbodiimide or uretonimine groups may be employed in conjunction with the organometallic complexes of the invention as well. Further blocked polyisocyanates, like the reaction product of a phenol or an oxime and a polyisocyanate, may be used, having a deblocking temperature below the temperature applied when using a polyisocyanate composition.

The organic polyisocyanate useful with the organometallic composition of the invention may also be an isocyanate-ended prepolymer made by reacting an excess of a diisocyanate or higher functionality polyisocyanate with a polyol.

Water-emulsifiable organic polyisocyanates like those described in UK patent no. 1 444 933, in European patent publication no. 516 361 and in PCT patent publication no. 91/03082 can also be used.

Mixtures of isocyanates may be used in conjunction with the organometallic composition of the invention, for example a mixture of tolylene diisocyanate isomers such as the commercially available mixtures of 2,4- and 2,6-isomers and also the mixture of di- and higher polyisocyanates. Polyisocyanate mixtures may optionally contain monofunctional isocyanates such as p-ethyl phenylisocyanate.

Such mixtures are well-known in the art and include the crude phosgenation products containing methylene bridged polyphenyl polyisocyanates, including diisocyanate, triisocyanate and higher polyisocyanates together with any phosgenation by-products.

Preferred isocyanates to be used in conjunction with the organometallic complexes of the present invention are those wherein the isocyanate is an aromatic diisocyanate or polyisocyanate of higher functionality such as a pure diphenylmethane diisocyanate or a mixture of methylene bridged polyphenyl polyisocyanates containing diisocyanates, triisocyanates and higher functionality polyisocyanates.

Methylene bridged polyphenyl polyisocyanates are well known in the art. They are prepared by phosgenation of corresponding mixtures of polyamines. For convenience, polymeric mixtures of methylene bridged polyphenyl polyisocyanates containing diisocyanate, triisocyanate and higher functionality polyisocyanates are referred to hereinafter as polymeric MDI. Polyisocyanates suitable for use with the organometallic complexes of the invention include SUPRASEC™ DNR, SUPRASEC™ 2185, RUBINATE™ M and RUBINATE™ 1840, all available from Huntsman ICI Polyurethanes.

Preferably the polyisocyanate is liquid at room temperature.

Conventional release agents can be added to or used in combination with a polyisocyanate composition containing a titanium, zirconium or hafnium complex according to the present invention.

In such compositions the conventional release agent is present in an amount varying between 0.2 and 10%, preferably between 0.5 and 6% and most preferably between 1 and 3% by weight based on the polyisocyanate whereas the titanium, zirconium or hafnium complex is preferably present in an amount varying between 0.2 and 4%, most preferably between 0.2 and 2% by weight based on the polyisocyanate.

Examples of conventional release agents include polysiloxanes, saturated or unsaturated fatty acids (such as oleic acid) or fatty acid amides or fatty acid esters and polyolefin waxes.

Preferred conventional release agents to be used in polyisocyanate compositions containing the organometallic complexes according to the present invention are polyolefin waxes or mixtures of polyolefin waxes, especially functionalised polyolefin waxes, which are dispersible in an aqueous medium to form an aqueous emulsion. More preferably, the polyolefin waxes are selected from oxidised polyethylene waxes and oxidised polypropylene waxes.

A preferred method for using the release agent is to apply the emulsion to the surface of the polyisocyanate treated lignocellulosic material or to the press metal surface prior to hot pressing the combination.

When used, an aqueous emulsion of the polyolefin wax should normally contain a sufficient amount of the polyolefin wax to provide a coverage of about 0.01 to about 1, and preferably about 0.02 to about 0.5 mg of the polyolefin wax per $cm^2$ of lignocellulosic material or press metal surface. Generally, lower levels of polyolefin wax are preferred as they are more cost effective. When taking the emulsifiers into account, the aqueous emulsions will usually contain about 0.2 to about 10%, preferably about 0.3 to about 5% by weight of total solids. The emulsions are usually prepared at 30 to 40% total solids, transported to the point of use and then diluted with water to the desired concentration.

It has been found that the polyolefin wax emulsion, when used in combination with polyisocyanate compositions containing organometallic compositions of the present invention, may be usefully applied to the lignocellulosic material or press metal surface in an amount equivalent to 8 to 14 mg per $cm^2$.

A particularly preferred polyethylene wax emulsion which can be used in a process in combination with an organometallic composition of the present invention in combination with a polyisocyanate is Rubilon™ 603 or Rubilon™ 605, both available from Imperial Chemical industries.

A particularly preferred polypropylene wax emulsion which can be used in a process in combination with an organometallic composition of the present invention in combination with a polyisocyanate is ME 42040 available from Michelman Inc. of Cincinnati, Ohio.

In order to further improve the storage stability of a polyisocyanate composition containing an organometallic composition of the present invention a diluent may be added to the composition. Suitable diluents include plasticizers of the type mentioned in "Taschenbuch der Kunststoff-Additive", Ed. by R. Gachter and H. Muller, Carl Hanser Verlag Munchen, third edition, 1989. Preferred diluents are phthalates, aliphatic carboxylates, fatty acid esters, linseed oil and soybean oil. A particularly preferred diluent is Priolube 1403 available from Unichema being methyloleate. These diluents are added in amounts of from 1 to 40 parts by weight per 100 parts by weight of polyisocyanate and preferably in amounts of from 1 to 15 parts by weight per 100 parts by weight of polyisocyanate.

A composition containing an organometallic composition of the present invention and a polyisocyanate may further comprise conventional additives such as flame retardants, lignocellulosic preserving agents, fungicides, waxes, sizing agents, fillers, surfactants, thixotropic agents and other binders like formaldehyde condensate adhesive resins and lignin (optionally in combination with a lignin solvent such as described in PCT Patent Application No. EP 96/00924).

A particularly preferred additive to be used in a polyisocyanate composition containing an organometallic composition of the present invention is a coupling agent such as an organofunctional silane (for example, Dynasylan AMEO, available from Huels). Adding such a coupling agent to the polyisocyanate composition leads to improved board properties. The organo-functional silane coupling agents are used in amounts ranging from 0.01 to 3%, preferably from 0.1 to 2% by weight based on the polyisocyanate.

The organometallic composition of present invention can be used in a process for preparing lignocellulosic bodies by bringing lignocellulosic parts into contact with a polyisocyanate composition containing the organometallic composition of the present invention and pressing this combination.

A typical process comprises the steps of
a) bringing said lignocellulosic material in contact with a polyisocyanate composition containing an organometallic composition of the present invention and,
b) subsequently allowing said material to bind.

The lignocellulosic bodies are prepared by bringing the lignocellulosic parts into contact with a polyisocyanate composition by means such as mixing, spraying and/or spreading the composition with/onto the lignocellulosic parts and by pressing the combination of the polyisocyanate composition and the lignocellulosic parts, preferably by hot-pressing, normally at 150° C. to 250° C. and 2 to 6 MPa specific pressure. Such binding processes are commonly known in the art.

In wafer-board manufacture the lignocellulosic material and the polyisocyanate composition may be conveniently mixed by spraying the present polyisocyanate composition on the lignocellulosic material while it is being agitated.

As described hereinbefore, in a preferred process, a release agent, which is preferably an aqueous emulsion of a polyolefin wax, is applied to the surface of the polyisocyanate treated lignocellulosic material or to the press metal surface prior to hot pressing the combination.

The lignocellulosic material after treatment with the polyisocyanate composition containing an organometallic composition according to the invention is placed on caul plates made of aluminium or steel which serve to carry the furnish into the press where it is compressed to the desired extent usually at a temperature between 150° C. and 250° C.

While the process is particularly suitable for the manufacture of wafer-board known extensively as oriented strand board and will be largely used for such manufacture, the process may not be regarded as limited in this respect and can also be used in the manufacture of medium density fiberboard, particle board (also known as chipboard) and plywood.

Thus the lignocellulosic material used can include wood strands, wood-chips, wood fibers, shavings, veneers, wood wool, cork, bark, sawdust and like waste products of the wood working industry as well as other materials having a lignocellulosic basis such as paper, bagasse, straw, flax, sisal, hemp, rushes, reeds, rice hulls, husks, grass, nutshells and the like. Additionally, there may be mixed with the lignocellulosic materials other particulate or fibrous materials such as ground foam waste (for example, ground polyurethane foam waste), mineral fillers, glass fiber, mica, rubber, textile waste such as plastic fibers and fabrics.

When the polyisocyanate composition containing the organometallic composition of the invention is applied to the lignocellulosic material, the weight ratio of polyisocyanate/lignocellulosic material will vary depending on the bulk density of the lignocellulosic material employed. Therefore, the polyisocyanate compositions may be applied in such amounts to give a weight ratio of polyisocyanate/lignocellulosic material in the range of 0.1:99.9 to 20:80 and preferably in the range of 0.5:99.5 to 10:90.

If desired, other conventional binding agents, such as formaldehyde condensate adhesive resins, may be used in conjunction with the polyisocyanate composition containing the organometallic composition.

More detailed descriptions of methods of manufacturing wafer-board and similar products based on lignocellulosic material are available in the prior art. The techniques and equipment conventionally used can be adapted for use with polyisocyanate compositions containing organometallic compositions of the present invention.

Polyisocyanate compositions containing organometallic compositions of the present invention are extremely effective in minimising unwanted adhesion to caul plates, press plates and other surfaces with which the treated lignocellulosic material may come into contact. Their storage stability and release performance is improved compared to polyisocyanate compositions of the prior art, as well as the obtained board properties. Also the flash point of the complexes of the present invention are relatively high, enabling them to be stored and handled more easily that materials having lower flash points.

The sheets and moulded bodies produced from the polyisocyanate compositions containing organometallic compositions of the present invention have excellent mechanical properties and they may be used in any of the situations where such articles are customarily used.

The organometallic compositions of the invention are also useful in other applications in which it is desired to effect curing of isocyanate groups in a polyurethane. Such other applications include coatings, e.g. decorative and industrial coatings for protection of wood, metals, plastics, glass, ceramics and other surfaces, including coatings subjected to heat. For use in higher temperature applications it may be advantageous to use an acetoacetate ester of an alcohol which has a high boiling point, e.g. above 200° C., such as an acetoacetate ester of an alcohol having at least 7 carbon atoms. Other applications include the manufacture of composite materials in which polyurethane binders are used, such as oriented strand board (OSB), medium-density fiberboard (MDF) or plywood. Still further applications may be found in composites, adhesives and foams and thermoplastic polyurethanes for use in automotive applications or footwear.

The invention is illustrated but not limited by the following examples.

EXAMPLE 1

Preparation of Precomplex Material A

A reactor was charged with tetraisopropyl titanate (1400 kg, Tilcom® TIPT from ICI Vertec). Ethylacetoacetate (EtAcAc) (1282 kg) was then added with stirring. The resulting product was a pale red liquid. The displaced alcohol (580 kg, isopropanol) was then removed by evaporation to leave a red liquid, precomplex A (2090 kg), di(2-propyloxy)titanium bis(ethylacetoacetate).

EXAMPLE 2

Preparation of Complex According to the Invention

Precomplex A (423.88 g) was stirred with 260.41 g of 2-ethyl hexanol and then distilled under vacuum to remove isopropanol until a constant weight was obtained. The product was di(2-ethylhexyloxy)titanium bis(ethylacetoacetate). 325 g of Et AcAc was added and the resulting product was a red mobile liquid, having a flash point of 68° C. as measured by the Gallenkamp Auto Flash AF3 using the method described in the Gallenkamp manual DET 284-488E issue III.

EXAMPLE 3

Preparation of Complex According to the Invention

The method described in Example 2 was followed but 260.7 g of iso octanol (2,4,4 trimethyl 1 pentanol) was substituted for the 2-ethyl hexanol. The resulting product, di(2,4,4-trimethyl-1-pentyloxy)titanium bis(ethylacetoacetate) with about 2.5 moles excess Et AcAc was a red mobile liquid, having a flash point of 58° C.

EXAMPLE 4

Comparison

Example 2 was repeated using 148 g of iso-butanol instead of 2-ethyl hexanol to produce di(2,2-dimethyl-1-ethyloxy)titanium bis(ethylacetoacetate). The resulting product was a clear orange/red mobile liquid having a flash point of 56° C.

EXAMPLE 5

Comparison

A reactor was charged with 283 g tetra(n-propyl)titanate. EtAcAc (260 g) was then added with stirring. The displaced alcohol (139 g, n-propanol) was then removed by evaporation until a constant weight was obtained to leave a yellow-orange liquid, di(n-propyloxy)titanium bis(ethylacetoacetate). 325 g of Et AcAc was added and the resulting product was a clear orange/red liquid, having a flash point of 46° C.

EXAMPLE 6

Comparison 325 g of Et AcAc was added to 426 g of precomplex A and the resulting product was a clear orange/red liquid, having a flash point of 49° C.

EXAMPLE 7

Comparison of Viscosity of Polyisocyanate Containing Complexes According to the Invention The products were evaluated by preparing a number of compositions comprising 100 g by weight of polyisocyanate (SUPRASEC DNR, available from Huntsman ICI Polyurethanes) and the indicated amount of the samples prepared in Examples 2–6. Each composition contained the same concentration of the complex. The compositions were then stored at 45° C. and the viscosity tested by means of a Brookfield DV-II Programmable Viscometer (following the Operating instructions found in the Brookfield Operating Instructions Manual No M/97-164-B299 ) at various intervals up to 85 days. The results are shown in the Table show that the titanates which raise the viscosity of the polyisocyanates least are those of Examples 2, 3 and 5, but of these only those of the invention have a flash point which is >50° C.

What is claimed is:

1. An organometallic composition comprising a complex of at least one orthoester of a metal having a formula $M(ROAcAc)_x, (OR')_y$ in which
   a) M is selected from the group consisting of titanium, zirconium and hafnium;
   b) ROAcAc denotes an ester of an alcohol ROH, in which R comprises an (optionally substituted) $C_{1-30}$ cyclic, branched or linear, alkyl, alkenyl, aryl or alkyi-aryl group or a mixture thereof, with acetoacetic acid;
   c) OR' is the residue of an alcohol R'OH in which R' comprises an (optionally substituted) $C_{7-30}$ cyclic, branched or linear, alkyl, alkenyl, aryl or alky-aryl group or a mixture thereof, and
   d) x and y are each in the range 1–3 and x+y=4.

2. An organometallic composition as claimed in claim 1, wherein R comprises an optionally substituted $C_7$–$C_{30}$ cyclic, branched or linear, alkyl, alkenyl, aryl or alkyl-aryl group or a mixture thereof.

3. An organometallic composition as claimed in claim 1, wherein R comprises an optionally substituted $C_1$–$C_6$ cyclic, branched or linear, alkyl, alkenyl, aryl or alkyl-aryl group or a mixture thereof.

4. An organometallic composition as claimed in claim 1, wherein R' comprises an optionally substituted $C_7$–$C_{18}$ cyclic, branched or linear, alkyl, alkenyl, aryl or alkyl-aryl group or a mixture thereof.

5. An organometallic composition as claimed in claim 4, wherein R' comprises an optionally substituted $C_7$–$C_{12}$ alkyl group.

6. An organometallic composition as claimed in claim 1, wherein R' and/or R contains at least one bromine, chlorine or fluorine atom.

7. An organometallic composition as claimed in claim 1, wherein M is titanium and the molar ratio of titanium to acetoacetate ester in the composition is in the range 1:2.5 to 1:10.

8. An organometallic composition as claimed in claim 1, wherein M is either hafnium or zirconium and the molar ratio of M to acetoacetate ester in the composition is in the range 1:4 to 1:10.

9. An organometallic composition as claimed in claim 1, wherein the composition comprises free acetoacetate ester.

10. An organometallic composition as claimed in claim 9, wherein said free acetoacetate ester is present in an amount to provide 0.5–10 moles free ester per mole of metal.

11. An organometallic composition as claimed in claim 10, wherein said free acetoacetate ester is present in an amount to provide 1–5 moles free ester per mole of metal.

12. An organometallic composition as claimed in claim 1, which is prepared by trans-esterification by R'OH of

|  |  |  | Viscosity (cP) at 25° C. | | | |
|---|---|---|---|---|---|---|
| Complex | Flash pt (° C.) | weight added (g) | Day 0 | Day 21 | Day 54 | Day 85 |
| Example 2 | 68.0000 | 0.6300 | 220.0000 | 366.0000 | 518.0000 | 828.0000 |
| Example 3 | 58.0000 | 0.6400 | 220.0000 | 430.0000 | 564.0000 | 774.0000 |
| Example 4 (comp) | 56.0000 | 0.5500 | 220.0000 | 376.0000 | 568.0000 | 1044.0000 |
| Example 5 (comp) | 46.0000 | 0.5100 | 220.0000 | 416.0000 | 520.0000 | 908.0000 |
| Example 6 (comp) | 49.0000 | 0.5300 | 220.0000 | 364.0000 | 580.0000 | 1296.0000 | titanium, zirconium or hafnium compounds having the general formula $M(OR")_2(ROAcAc)_x$ in which M is Ti, Zr or Hf and R" is a substituted or unsubstituted, cyclic, branched or linear, alkyl, alkenyl, aryl or alkyl-aryl group or mixtures thereof.

13. An organometallic composition as claimed in claim 12, wherein R" comprises methyl, ethyl, isopropyl, n-propyl, iso-butyl or n-butyl.

14. An organometallic composition as claimed in claim 1 which has a flash point greater than 50° C.

15. A method of making an organometallic composition as claimed in claim 1 comprising the steps of:
   a) mixing together a metal tetra-alkoxide, $M(OR")_4$ with an acetoacetate ester, ROAcAc, in which R and R" are each selected from a (substituted or unsubstituted) cyclic, branched or linear, alkyl, alkenyl, aryl or alkyl-aryl group or mixtures thereof and M is selected from titanium, hafnium or zirconium, such that at least 2 moles of ROAcAc is present in the mixture for each mole of $M(OR")_4$
   b) removing from the mixture the alcohol R"OH formed during the reaction;
   c) and then adding to said mixture an alcohol R'OH in which R' comprises an (optionally substituted) $C_{7-30}$ cyclic, branched or linear, alkyl, alkenyl, aryl or alkyl-aryl group or a mixture thereof;
   d) removing from the mixture the alcohol R"OH formed during the reaction; and optionally
   e) adding a further quantity of ROAcAc such that when M is titanium the molar ratio of titanium to total acetoacetate ester in the composition is in the range 1:2.5 to 1:10 and when M is either hafnium or zirconium the molar ratio of M to total acetoacetate ester in the composition is in the range 1:4 to 1:10.

16. A curable mixture comprising an organic isocyanate compound or mixture of organic isocyanate compounds and an organometallic composition as claimed in claim 1.

17. A curable mixture as claimed in claim 16, wherein said isocyanate compound is an aliphatic or aromatic diisocyanate, a modified polyisocyanate containing isocyanurate, carbodiimide or uretonimine groups, an isocyanate-ended prepolymer made by reacting an excess of a diisocyanate or higher functionality polyisocyanate with a polyol; a water-emulsifiable organic polyisocyanate or a mixture of two or more of the aforementioned polyisocyanates.

18. A curable mixture as claimed in claim 17, wherein said isocyanate is selected from hexamethylene diisocyanate, m- and/or p-phenylene diisocyanate, tolylerie-2,4-or tolylene-2,6-diisocyanate, diphenylmethane-4,4'-diisocyanate, chlorophenylene-2,4-diisocyanate, naphthylene-1,5-diisocyanate, diphenylene-4,4'-diisocyanate, 4,4'-diisocyanate-3,3'-dimethyl-diphenyl, 3-methyldiphenylmethane-4,4'-di-isocyanate and diphenyl ether diisocyanate, cyclohexane-2,4- and/or -2,3-diisocyanate, 1-methylcyclohexyl-2,4- and/or -2,6-diisocyanate, bis-(isocyanatocyclohexyl)methane, 2,4,6-triisocyanatotoluene and 2,4,4-tri-isocyanatodiphenylether.

19. A lignocellulosic body comprising a lignocellulosic material, and a polyisocyanate composition containing an organometallic composition as claimed in claim 1.

20. A process for the preparation of a lignocellulosic body comprising the steps of
   a) bringing a lignocellulosic material in contact with a polyisocyanate composition containing an organometallic composition as claimed in claim 1, and
   b) subsequently allowing said material to bind.

* * * * *